US00PP08185P

United States Patent [19]

Negre

[11] Patent Number: Plant 8,185

[45] Date of Patent: Mar. 23, 1993

[54] SPRAY CARNATION NAMED OPALE

[75] Inventor: Yvon Negre, Paris, France

[73] Assignee: Laboratoire de Physiologie Vegetale, Paris, France

[21] Appl. No.: 791,115

[22] Filed: Nov. 12, 1991

[51] Int. Cl.[5] ..... A01H 5/00

[52] U.S. Cl. ..... Plt./70.5

[58] Field of Search ..... Plt./70.5, 70.6, 71.1, Plt./72.1

*Primary Examiner*—Howard J. Locker

*Attorney, Agent, or Firm*—Tilton, Fallon, Lungmus & Chestnut

[57] ABSTRACT

A new variety of spray carnation particularly distinguished by its very large flowers which are borne in a cluster, the petals of which are light pink in color and greenish at the base, the blooming habit being both recurrent and profuse during the blooming seasons of Spring and Fall. This plant has a vigorous, upright growth habit and moderately abundant foliage.

1 Drawing Sheet

BACKGROUND OF THE NEW PLANT

My new carnation cultivar is the result of breeding efforts carried on by us as LaLonde, Les Maures, France, this new plant originated as a seedling produced from my crossing of selected and individually identified plants growing among my stock of plants maintained at La Londe for breeding purposes. This particular seedling was selected by me for propagation and tests because of its very unusual flower coloration and was reproduced under my direction at La Londe by means of cuttings. This propagation had favorable results with respect to retention of the novel characteristics of the parent plant and successive propagation through several generations established definitively that the novel and distinctive characteristics of the parent plant are fully retained from generation to generation and appear to be firmly fixed.

DESCRIPTION OF THE DRAWING

My new spray carnation variety is illustrated by the accompanying photographic drawing which, in full color, shows a typical arrangement of buds and flowers in various stages of opening, the colors shown being as nearly true to those specified herein as is reasonably possible to obtain by conventional photographic procedures.

DESCRIPTION OF THE NEW PLANT

The following is a detailed description of my new spray carnation cultivar with the color designations specified being according to The R.H.S. Color Chart of The Royal Horticultural Society of London, England.

THE PLANT

Origin: Seedling.

Parentage:

*Seed parent.*—No. 80 MC 16 (unpatented).

*Pollen parent.*—No. 414 MFC (unpatented). Both varieties are identified in my breeding records maintained at my nursery in La Londe, France.

Classification:

*Botanic.*—*Dianthus caryophyllus.*

*Commercial.*—Spray carnation.

Form: Erect bush having at least four stems emitted near the ground.

Height: About 93.6 cm. in average.

Main stem: Less than 15 cm. due to pinching.

Branching character: This plant is moderately branched.

Growth habit: Vigorous, upright and rigid.

Foliage:

*Quantity.*—Moderately abundant.

*Number of leaves.*—More than 120.

*Size of leaf.*—About 14.9 cm. long and 0.87 cm. wide at the seventh node.

*Leaf shape.*—Spindle shaped with curved margins.

*Texture.*—Leathery.

*Color.*—Upper side — 137-A. Under side — 137-A.

Ribs and veins: Hardly noticeable.

Rachis: Hardly noticeable.

THE BUD

Size:

*Diameter.*—Approximately 1.5 cm.

*Length.*—Approximately 2.7 cm.

Form: Cylindrical.

Rate of opening: Normal.

Color of petals:

*When sepals first divide.*—Between 56-A and 56-D.

*When petals begin to unfurl.*—The same as in full bloom.

Sepals:

*Number.*—4 to 5.

*Shape.*—The sepals are hooded over the bud before dividing and curl back as the flower petals unfurl. The sepals are joined together at the lower part and are sharp pointed at the apex.

*Color.*—Inside — 149-D and 137-D. Outside — 137-B and 144-B.

Striae: Longitudinal.

Calyx:

*Shape.*—Cylindrical.

*Size.*—Long.

*Splitting.*—The calyx does not split.

*Aspect.*—Smooth.

THE FLOWER

Blooming habit: Recurrent and profuse during the mid-season of both Spring and Fall.

Size of bloom: Very large.

*Diameter.*—About 6.6 cm. in average.

*Depth.*—About 5.1 cm. in average.

Borne: In a cluster.
Shape:
*When bloom first opens.*—High centered.
*When bloom matures.*—Dome shaped.
Petalage:
*Number of petals.*—Approximately 45 in average.
*Arrangement.*—Imbricated.
*Form.*—Fan-shaped with rounded edges, not serrated.
*Texture.*—Leathery.
*Appearance.*—Satiny.
*Color.*—Outer petal — between 55-D and 56-A. Base — greenish. Reverse side — between 56-A and 56-D. Inside petal — about the same as the outer petals.
Petaloids:
*Number.*—Less than 6.
*Size.*—Smaller than petals.
*Color.*—The same as petals.
Flower stem:
*Length.*—About 75.4 cm. in average.
*Color.*—137-B.
*Character.*—Upright and rigid.
Persistence: The petals hang on and dry.
Fragrance: Perceptible.
Disease resistance: Good resistance to *Fusarium oxysporum* as observed at Antibes, France.
Lasting quality:
*As a cut flower.*—At least 10 days with vase keeping.

THE REPRODUCTIVE ORGANS

Stamens:
*Number.*—3 to 9.
*Arrangement.*—Around the ovary.
*Anthers.*—Size: Less than 0.4 cm. Color: Whitish.
Pistils:
*Number.*—2 to 4.
*Styles.*—Length: 2.9 cm. Color: Whitish.
*Stigmas.*—Color: Whitish.
Character of the ovaries: The ovary is slightly ribbed.

This new variety most nearly resembles Lonwadec (U.S. Plant Pat. No. 6,210), but is distinguished therefrom by a longer stem, a light pink color, a large flower with a round petal and resistance to *Fusarium oxysporum.*

I claim:

1. A new and distinct spray carnation plant substantially as herein shown and described, characterized by its recurrent and profuse production of large flowers which are light pink in color and by the petals which are round at the outer margin.

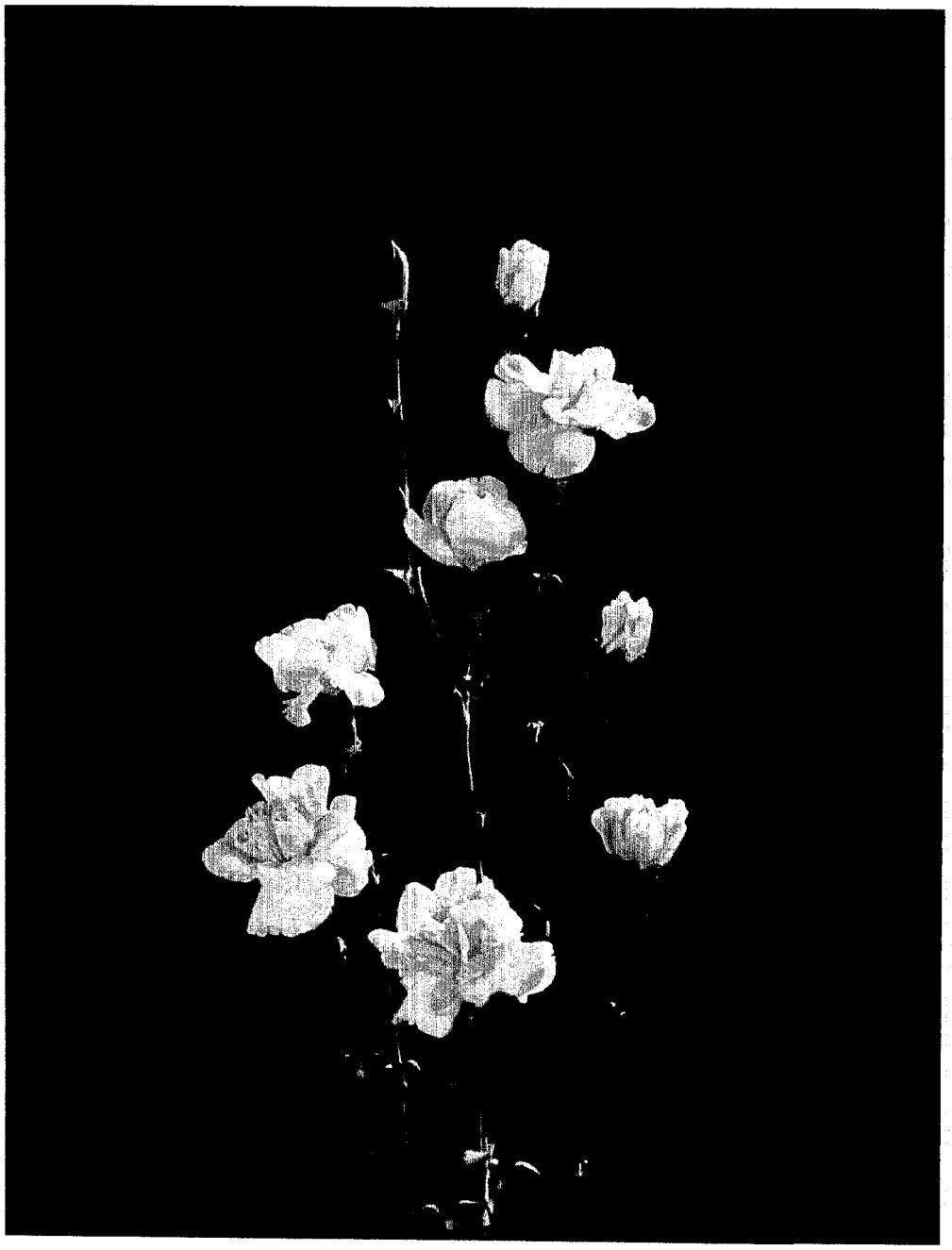

* * * * *